United States Patent [19]

Maas

[11] 3,950,694
[45] Apr. 13, 1976

[54] INSTALLATION FOR THE DETECTION AND PROCESSING OF ELECTRICAL SIGNALS

[75] Inventor: Michael Maas, Erlangen, Germany

[73] Assignee: Siemens Aktiengesellschaft, Erlangen, Germany

[22] Filed: Dec. 6, 1974

[21] Appl. No.: 530,355

[30] Foreign Application Priority Data
Dec. 13, 1973 Germany............................ 2362039

[52] U.S. Cl. ......... 323/16; 128/2.06 B; 128/2.06 F; 307/235 R; 328/162; 328/165
[51] Int. Cl.² ...................... G05F 1/00; A61B 5/04
[58] Field of Search ........ 323/8, 16, 17; 307/235 R, 307/237, 264; 328/162, 165; 128/2.06 B, 2.06 F, 2.06 R, 2.05 T, 419 R, 419 PT, 419 PG

[56] References Cited
UNITED STATES PATENTS

| | | | |
|---|---|---|---|
| 3,387,222 | 6/1968 | Hellwarth, Jr. | 307/235 R |
| 3,517,212 | 6/1970 | Nelson | 307/235 R |
| 3,554,188 | 1/1971 | Lasch et al. | 128/2.06 F |
| 3,721,230 | 3/1973 | Ziernicki | 128/2.06 B |
| 3,804,979 | 4/1974 | Knowles | 307/235 R |

Primary Examiner—Gerald Goldberg
Attorney, Agent, or Firm—Haseltine, Lake & Waters

[57] ABSTRACT

An installation for the detection and, respectively, processing of electrical signals, in particular, physiological measuring signals, for example EKG, including a damping arrangement with an adjusting element for the setting of desired damping degrees for the signals. The adjusting element of the damping arrangement has a control element associated therewith which is connected to a signal scanning installation, detects the frequency at which the significant amplitude values occur in the signal and generates an electrical signal in conformance with frequency of occurrence of these values; and the control element sets the adjusting element of the damping arrangement in dependence upon this signal in such a manner so that the damping degree for the electrical signals is increased until the frequency of occurrence of the significant amplitude values falls below a predetermined minimum value.

5 Claims, 1 Drawing Figure

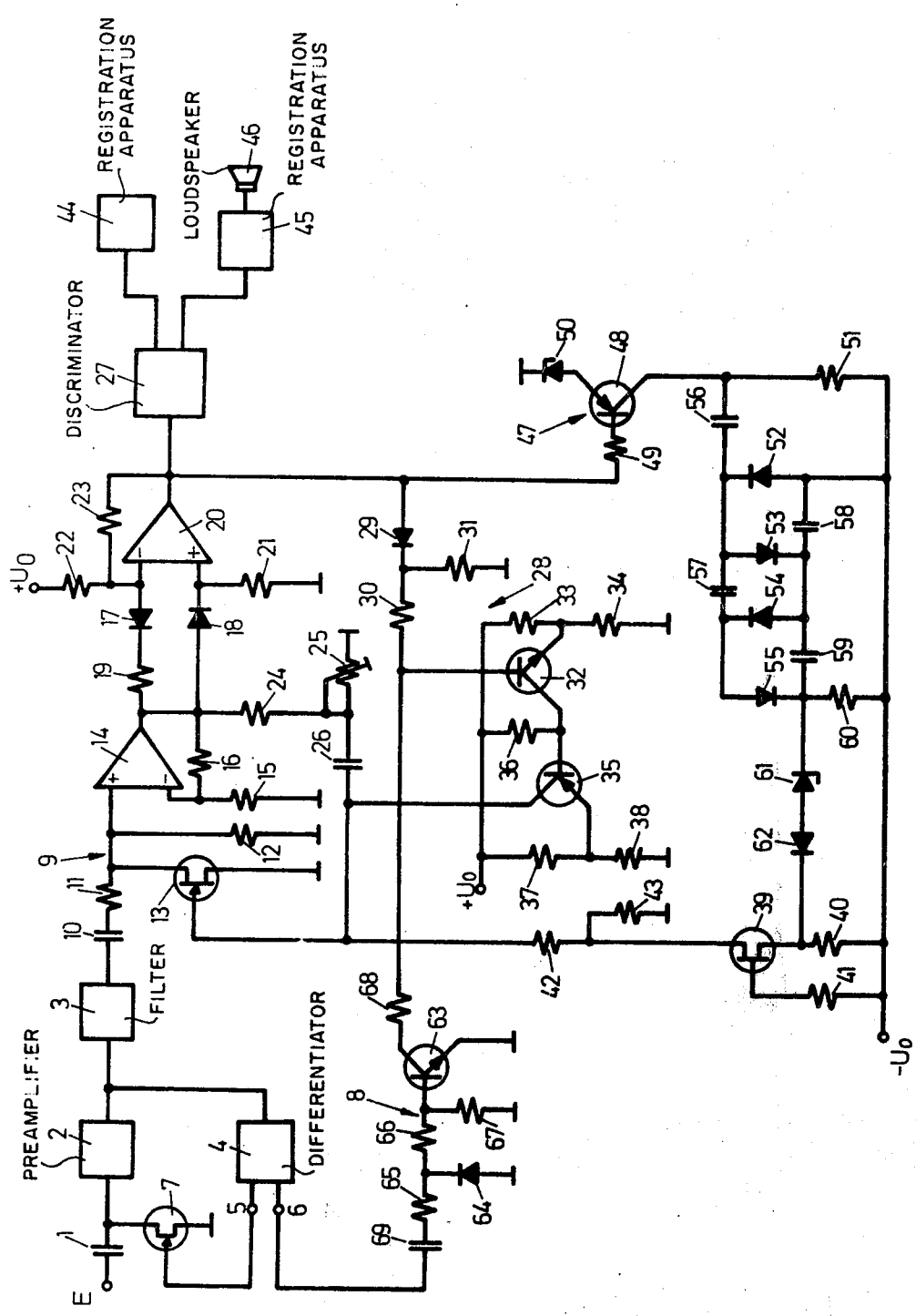

INSTALLATION FOR THE DETECTION AND PROCESSING OF ELECTRICAL SIGNALS

FIELD OF THE INVENTION

The present invention relates to an installation for the detection and, respectively, processing of electrical signals, in particular, physiological measuring signals, for example EKG, including a damping arrangement with an adjusting element for the setting of desired damping degrees for the signals.

DISCUSSION OF THE PRIOR ART

Electrical signals, particularly physiological measuring signals, frequently have static voltages superimposed thereon which continually occur and, in particular at high amplitudes, may lead to erroneous results in the processing of the signals. For example, it may frequently occur during the EKG processing that in the selection of the R-displays or waves by means of threshold discriminators or the like, especially high static amplitudes may similarly exceed the threshold of the threshold discriminator, and be falsely evaluated by the discriminator as genuine R-displays. In this instance, typical static voltages are especially the known power supply hum. Since the above-mentioned static voltages, and in particular the power supply hum, may lie within approximately the same frequency range as also the electrical signals, any blacking-out of these static voltages from the electrical signals is either completely impossible or only possible to an insufficient extent with the use of commonly known filters.

SUMMARY OF THE INVENTION

Accordingly, it is an object of the present invention to provide an installation for the detection and, respectively, processing of electrical signals, in particular physiological measuring signals such as EKG, in which static voltages of the previously mentioned type, and especially power supply hum, may be clearly eliminated from the measuring signal through employment of the simplest means, so as to no longer be disturbingly effective at least during the continued signal processing.

The foregoing object is inventively achieved with an installation of the previously mentioned type; wherein the adjusting element of the damping arrangement has a control element associated therewith which is connected to a signal scanning installation detects the frequency at which the significant amplitude values occur in the signal and generates an electrical signal in conformance with frequency of occurrence of these values; and that the control element sets the adjusting element of the damping arrangement in dependence upon this signal in such a manner so that the damping degree for the electrical signals is increased until the frequency of occurrence of the significant amplitude values falls below a predetermined minimum value.

The present invention derives the solution of the foregoing object from the knowledge to at static voltages of the mentioned type, for example, power supply hum, the static voltages occur much more frequently within the same intervals as, for example, do such amplitudes in electrical signals which are interesting for further processing (for example, R-display waves in EKG signals). Accordingly, if an electrical utilization signal, for example an EKG signal, actually has such a static voltage superimposed thereon, then the presence of this static voltage is detected by means of the signal scanning arrangement due to the increased frequency of occurrence of the signal values lying in the range of these static amplitudes. The resultingly generated output signal of the signal scanning arrangement effects through the control element the adjustment or setting of the adjusting element of the damping arrangement towards higher damping values for the electrical signal. When such a damping degree is finally reached, that frequency of occurrence of the significant amplitude values falls below a predetermined minimum value, then the static voltages with their amplitudes also lie below these significant amplitude values. A threshold discriminator which, as required, is also set for the electrical signals will thereby only detect the amplitudes of the electrical signal which lies above these amplitude values (for example, for EGK signals unambiguously only the R-displays).

In a preferred embodiment of the invention, the signal scanning arrangement encompasses a threshold discriminator whose threshold is set to a value which lies in the range of the expected highest amplitude of the mentioned, as occasioned superimposed on the electrical signal, continually appearing static voltage, for example power supply hum, and which further contains a frequency voltage converter generating an output signal in conformance with the frequency of exceeding the threshold of the threshold discriminator, which forms the control signal for the control installation for the control of the adjusting element of the damping arrangement. When the damping arrangement utilizes a voltage divider with a field-effect-transistor for the setting of desired damping degrees through controlled transistor resistance variation, then in a further embodiment of the invention there is further provided control transistor with the field-effect transistor, which preferably is also a field-effect transistor, whereby the control transistor, at an increasing output voltage of the signal scanning arrangement, controls the increasing resistance values of the field-effect transistor of the damping arrangement corresponding to the damping degree of the damping arrangement.

BRIEF DESCRIPTION OF THE DRAWING

Further advantages and details of the invention may now be ascertained from the following description of an exemplary embodiment (for example, in connection with EKG-processing), taken in conjunction with the accompanying single FIGURE of the drawing which schematically illustrates a circuit diagram of the invention.

DETAILED DESCRIPTION

In the installation as shown in the FIGURE of the drawing, EKG signals are applied to an input E. From there they are separately transmitted through an input capacitance 1, as well as through a first preprocessing element 2 which, in the usual manner, includes a preamplifier, to respectively second and third preprocessing elements 3 and 4. The second preprocessing element 3 hereby incorporates the usual active band-pass filter with pulse frequencies of, for example, 4 Hz and 23 Hz. The band-pass filter is transmissive for QRS-complexes, as well as for P- and T-waves of the EKG, and also for flicker or scintillation waves. The third preprocessing element 4, in contrast therewith, for example, incorporates a differentiating element with a subsequent full-wave rectifier, amplitude discriminator, as well as a monostable flip-flop or stepping oscillator. If pacemaker impulses, for example, coincide with the EKG signals, then the preprocessing element 4 discriminates these due to their larger increase steepness at the subsequently awaited amplitude of the EKG signals (the R-displays) of comparable amplitude values so that an output signal is produced at the output 5 through the intermediary of the monostable flip-flop. This output signal serves as the drive-control impulse for a field-effect transistor 7, the latter of which is connected to the input of the preprocessing element 2, which is thereby controlled into a conductive condition for the shortcircuiting and the consequent elimination of the pacemaker impulses from the EKG. Concurrently with the drive-control impulse for the transistor 7, at the output 6 of the element 4 there is also generated an impulse for actuation of a threshold-frequency oscillator 8, which is described in greater detail hereinbelow.

The frequency-trimmed EKG signals which are received at the output of the preprocessing element 3 are than transmitted to the non-inverting input of an operational amplifier 14 through a high-pass filter 9 which includes a series capacitance 10 as well as a subsequent voltage divider for the EKG signals consisting of an ohmic series resistance 11, as well as an ohmic shunt resistance 12 with a parallel positioned field-effect transistor 13. The inverting input of this amplifier 14 thereby is connected, on the one hand, across the resistance 15 with the ground and, on the other hand, through the resistance 16 with the amplifier output. The resistances, as well as the capacitance of the high-pass filter 9, are collectively so dimensioned that for the switched-in transistor 13, the lower limiting frequency of the filter, 9 at a maximum dividing ratio for the voltage divider (maximum transmission damping of the filter), evidences a maximum value of approximately 8 Hz, and for the blocked transistor 13 at a minimum dividing ratio, the voltage divider (minimum transmission damping of the filter), evidences a minimum value of approximately 4 Hz.

The signals which appear at the output of the operation amplifier 14 are transmitted, on the one side, to a full-wave rectifier which is constructed of diodes 17 and 18, a series resistance 19, as well as an amplifier 20 with the switching resistances 21, 22, 23; and, on the other side transmitted through a voltage divider 24, 25 to a condenser 26. The amplifier 20 of the full-wave rectifier, at positive EKG signals, operates as a non-inverting and, conversely, at negative signals, as an inverting amplifier. Accordingly, it causes across the resistances 22, 23 which are applied to the voltage + $U_0$, a displacement of the zero line of the amplifier output signals in a negative direction for a constant amount. The amount of the zero displacement thereby is so selected, so that in the normal instance the R-displays of the EKG signals at the output of the full-wave rectifier at a conductive transistor 13 of the high-pass filter 9 still lies above the positive threshold (for example, + 1 volt) of a first threshold discriminator 27, as well as also lying for a blocked transistor 13 above a therewith comparably higher threshold (for example, + 4 volts) of a second threshold discriminator 28.

The first threshold discriminator 27 essentially consists of a monostable flip-flop, which generates an output signal upon the respective exceeding of its input threshold generates by the EKG signals. The second threshold discriminator 28 consists of a diode 29, a voltage divider 30, 31, as well as a base-emitter section of a transistor 32, inclusive of a voltage divider 33, 34 for the emitter bias voltage connected to this transistor on the emitter side thereof and lying at the voltage + $U_0$ voltage. The transistor 32 additionally, together with a further transistor 35 having switching resistance 36, 37, 38, forms a control voltage amplifier. This control voltage amplifier, in conjunction with the previously described condenser 26, generates a control voltage (which is supplied with a portion of the output voltage of the amplifier 14 for improved signal linearization) at the field-effect transistor 13 of the high-pass filter 9, which controls the transistor 13 in dependence upon the signal amplitudes at the input of the threshold discriminator 28 towards higher or lower resistance values. The dependence of the control upon the input signal of the threshold discriminator 28, which corresponds to the output signal of the full-wave rectifiers 17 to 23, is hereby obtained as follows:

When the EKG signal of the full-wave rectifiers 17 to 23 lies below the threshold of the threshold discriminator 28, then the condenser 26 is charged to a negative voltage value through a charging installation-$U_0$, 39, as well as 40 through 43 (wherein the element 39 represents a control field-effect transistor for the operative point control of the field-effect transistor 13 in the high-pass filter 9, and the elements 41 through 43 represent ohmic resistances), which as bias voltage-blocking value maintains the field-effect transistor 13 at a high resistance value. This resistance value is so selected through the bias voltage-blocking value, that flicker waves which pass through the high-pass filter 9 indicate an amplitude at the output of full-wave rectifiers 17 to 23 at an amplitude which, in all instances, still lies above the threshold of the threshold discriminator 27. When, in contrast therewith, the output signal of the full-wave rectifier 17 to 23 exceeds the threshold of the threshold discriminator 28 (this case is encountered at least during the occurrence of an R-display in the EKG), then the voltage of the voltage divider 33, 34 will inclusively exceed the switching voltages of the transistor 32, as well as that of diode 29. The transistor 32 becomes conductive and correspondingly controls the transistor 35 of the control voltage amplifier into a conductive condition. The condenser 26 thereby is rapidly discharged to a positive value across the collector-emitter section of the transistor 35 so that the field-effect transistor 13 in the high-pass filter 9 is equally rapidly regulated to lower resistance values. Through the herewith following increase in the transmission damping of the high-pass filter 9, the EKG signals at the output of the full-wave rectifiers are now extremely rapidly damped to such an extent, until the R-display or wave runs closely below the threshold value of the threshold discriminator 28. Concurrent with the increased damping, there follows an increase in the lower limit frequency of the high-pass filter 9 from approximately 4 Hz to approximately 8 Hz.

The control voltage amplifier 32, 35 through 38 thereby, in operative connection with the threshold discriminator 28, as well as the condenser 26 and through the field-effect transistor 13 in the high-pass filter 9, controls the frequency width and the transmission damping of the filter 9 so that, for a normal EKG (also at extensively oscillating amplitudes), the total EKG is damped such a value, whereby the R-displays or waves are levelled essentially to values closely below the threshold of the threshold discriminator 28. Through the concurrent displacement of the lower limit frequency of the highpass filter 9 in the direction of the frequency value which is significant for the R-display, there is additionally increased the amplitude distance between the R-display and the P- and, respectively, T-wave. At the threshold discriminator 27 there appear accordingly essentially only clear selected R-display amplitudes which, due to the regular exceeding of the threshold of the threshold discriminator 27, may be registered as genuine R-displays at an indicator or, respectively, registration apparatus 44. If in contrast therewith, flicker waves appear at the output of the full-wave rectifiers 17 to 27, then in the normal case, the amplitude thereof remains continually below the threshold of the threshold discriminator 28 (the amplitudes of flicker waves on an average are one-third of the R-display amplitude in the normal EKG). The condenser 26 is maintained at the bias voltage value of the field-effect transistor 13 (closing voltage value) due to the blocked transistor 35.

The high resistance value of the field effect transistor 13 causes that, on the one hand, the transmission damping value of the high-pass filter 9 is reduced to its minimum value and, concurrently, the lower limit frequency of the frequency values which are significant to the flicker waves is opened (reduction of the lower frequency to about 4 Hz). The flicker waves may thereby pass practically undamped through the high-pass filter 9. Correspondingly, the undamped amplitudes of the flicker waves at the output of the full-wave rectifiers 17 to 23 thereby still also lie above the threshold of the threshold discriminator 27. Since the flicker waves now relatively frequently exceed the threshold of the threshold discriminator 27, with the occurrence of the waves in opposition to the normal QRS complexes in EKG is, however, primarily discontinuous, due to occurrence frequency criterium at a concurrent occurrence discontinuity, the presence of the flicker waves may now be clearly recognized, for example, through the registration apparatus 45 and, in conformance therewith, an acoustic or any kind of alarm (for example, a loudspeaker 46) may be activated.

In addition to the two threshold discriminators 27 and 28, there is also connected to the output of the full-wave rectifiers 17 to 23, a third threshold discriminator 47 which includes the transistor 48, the base resistance 49, and the emitter-zener diode 50. This threshold discriminator 47, in contrast with the thresholds of the discriminators 27 and 28, evidences a very much lower signal threshold lying in the negative range (for example, at −3 volts). The threshold discriminator 47, on the output side thereof, is connected across a resistance 51 to a voltage multiplier (diode pump) having diodes 52 through 55, capacitances 56 through 59, as well as a load resistance 60. The output of this voltage multiplier, in turn, is coupled across a zener diode 61, as well as semi-conductor diode 62 directly to the source of the previously mentioned field-effect transistor 39 which serves as the operative point control transistor for the field-effect transistor 13 of the high-pass filter 9.

The threshold discriminator 47, together with the voltage multiplier 52 through 60, serves as a control voltage amplifier for the blacking-out of higher-frequency static which is continually superimposed on the EKG signals (for example, power supply hum). The blacking-out of the static functions herein as follows:

When that kind of static occurs in the EKG signal at the output of the full-wave rectifiers 17 to 23 (for example, power supply hum), then the amplitude of this static unequally frequently exceeds the threshold of the threshold discriminator 47 such as, for example, the R-display of the normal EKG. Detrimentally, within a short period, the transistor 48 is thus reversely controlled a number of times from a conductive into a blocked condition. At each new switching sequence of the transistor 48, a voltage increase occurs at the resistance 51 which effects the voltage multiplier in the sense in that, after a few switching pulses, there is formed a relatively high voltage at the load resistance 60 of the voltage multiplier. As soon as this voltage exceeds the zener voltage of the zener diode 61, as well as the switching voltage of diode 62, it exerts an effect on the field-effect transistor 13 across the control transistor 39 in a sense whereby this transistor 13 is so far regulated towards a positive bias voltage value and thereby to lower resistance values, until the amplitude of the static is regulated below the threshold of the threshold discriminator 47. By means of the threshold discriminator 47 with the subsequent voltage multiplier 52 through 60, as well as the operative point adjusting transistor 39 for the field-effect transistor 13 in the high-pass filter, the entire EKG signal is maintained so small from the beginning (initial damping), that a higher-frequency static of the previously mentioned type (for example, power supply hum) from the threshold discriminator 27 is not evalued as a phenomenon when it continuously occurs.

The already previously mentioned threshold-frequency oscillator 8 consists of a transistor 63, a diode 64, the resistances 65 through 68, as well as an input capacitance 69. If there appears a (negative) voltage impulse in the EKG signal at the output 6 of the element 4 due to the pacemaker impulses recognized in the preprocessing element 4, then the condenser 69 of the threshold-frequency oscillator is charged over to a negative value through the diode 64. After this impulse, the condenser 69 discharges across the base-emitter section of the transistor 63. The transistor 63 is hereby controlled for a predetermined time, preferably for 250 milliseconds, into a conductive condition. This has the effect that, for the same time period, meaning also for 250 milliseconds, the actuating threshold of the threshold discriminator 28, by means of resistances 68 and 30 which now operate as voltage dividers, is displaced towards higher values, preferably to double the normal value (from + 4 volts to approximately + 8 volts). This short-term threshold increase at each time after the occurrence of a pacemaker impulse has the advantage that immediately after, the heart action voltages occurring subsequent to pacemaker impulses with an amplitude which is inherently larger than the amplitude at self-excitation, are extensively damped within a short time. The danger that self-exciting heart action, which follows a heart action effected by pacemaker impulses, may be lost due to the long-durational strong damping at a low threshold of the threshold discriminator 28 (at + 4 volts), is thus no longer present.

While there has been shown what is considered to be the preferred embodiment of the invention, it will be obvious that modifications may be made which come within the scope of the disclosure of the specification.

What is claimed is:

1. In an installation for detection and processing of electrical signals, in particular physiological measuring signals such as EKG, including a damping arrangement having an adjusting element for the setting of desired damping degrees for the signals, the improvement comprising: a control element operatively associated with said adjusting element; and a signal scanning arrangement being connected to said control element; said damping arrangement including a voltage divider with a field-effect transistor for the setting of the desired damping degree through controlled transistor resistance variation; a control transistor being connected to said field effect transistor so as to control the latter, at an increasing output voltage of said signal scanning arrangement, towards higher resistance values corresponding to the damping degree of said damping arrangement; said signal scanning arrangement detecting the frequency at which significant amplitude values occur in the signal and generating an electrical signal in conformance with the frequency of occurrence of the values, said control element adjusting said adjusting element in dependence upon said last-mentioned electrical signal whereby the damping degree is increased for said electrical signals until frequency of occurrence of the significant amplitude values falls below a predetermined minimum value.

2. Installation as claimed in claim 1, said control transistor comprising a field-effect transistor.

3. Installation as claimed in claim 1, said signal scanning arrangement comprising a threshold discriminator having a threshold set at a value conforming to an expected highest amplitude of a continually occurring static voltage, such as power supply hum, superimposed on the electrical signal; said threshold discriminator including a transistor forming a threshold switch, said transistor adapted to be controlled into a conductive condition upon the transistor input voltage exceeding the switching voltage of said transistor inclusive the zener voltage of a zener diode located in the emitter circuit of said transistor; and a frequency voltage converter in said signal scanning arrangement adapted to generate an output signal in conformance with the exceeding of the threshold frequency of said threshold discriminator, said output signal forming a control signal of said control element for the control of the adjusting element of said damping arrangement.

4. Installation as claimed in claim 3, comprising a voltage multiplier including series capacitances and parallel diodes, said transistor being connected to said voltage multiplier across a collector resistance, said voltage multiplier forming said frequency voltage converter; and an output resistance having a voltage generated therein by said voltage multiplier increasing with the switching pulse of said second threshold discriminator.

5. Installation as claimed in claim 4, comprising diode switching means including a zener diode with a reverse-poled normal semiconductor diode, said output voltage of said voltage multiplier being connected to the source of said control transistor through said diode switching means, said control transistor controlling the field-effect transistor of said damping arrangement to higher resistance values for a period until the output signal of the voltage multiplier exceeds the switching voltage of said diode switching means.

* * * * *